United States Patent [19]

Sarnoff et al.

[11] 4,452,241

[45] Jun. 5, 1984

[54] PLURAL STATION RESUSCITATOR

[75] Inventors: Stanley J. Sarnoff; William R. Tarello, both of Bethesda; Claudio Lopez, Silver Spring, all of Md.; Rudolph S. Malooley, Annandale, Va.

[73] Assignee: Survival Technology, Inc., Bethesda, Md.

[21] Appl. No.: 383,962

[22] Filed: Jun. 1, 1982

[51] Int. Cl.³ .............................................. A62B 7/04
[52] U.S. Cl. ........................... 128/204.18; 128/205.19; 128/205.13; 128/203.28
[58] Field of Search ...................... 128/203.12, 203.28, 128/203.29, 204.18, 205.13, 205.14, 205.16, 205.19, 205.25

[56] References Cited

U.S. PATENT DOCUMENTS

| | | | |
|---|---|---|---|
| 2,969,789 | 1/1961 | Mosch | 128/205.14 |
| 3,721,239 | 3/1973 | Myers | 128/205.17 |
| 3,818,806 | 6/1974 | Fumagalli | 128/205.13 X |
| 3,995,626 | 12/1976 | Pearce | 128/204.18 X |
| 4,186,737 | 2/1980 | Valenta et al. | 128/203.28 |
| 4,193,406 | 3/1980 | Jinotti | 128/205.19 X |

*Primary Examiner*—Edward M. Coven
*Attorney, Agent, or Firm*—Cushman, Darby & Cushman

[57] ABSTRACT

Apparatus for resuscitating a plurality of patients comprising four face mask assemblies each of which is operable to be operatively connected with a patient so as to permit fresh air to be supplied to the lungs of such patient and four bellows assemblies actuated by a cam track rotated either by a suitable clutched electric motor or by hand crank for delivering successive volumes of fresh air under pressure to each face mask assembly at a desired cyclical frequency wherein each cycle includes said fresh air delivery as a minor part thereof. Each face mask assembly has operatively associated therewith (1) a stale air exhaust valve assembly for permitting air expelled from the lungs of each patient during the remaining major part of each cycle associated therewith to be exhausted to atmosphere, (2) a medicament injector for selectively supplying a respiratory medicament dosage into the fresh air delivered to each face mask assembly, and (3) a pressure gauge for indicating the operative pressure adjacent the face mask assembly so as to enable the operator to readily determine a bronchoconstrictive condition of a patient operatively connected with the associated face mask assembly so that the associated selective medicament injector is selected to deliver medicament only during the minor cycle part when the fresh air is delivered.

21 Claims, 9 Drawing Figures

PLURAL STATION RESUSCITATOR

This invention realtes to apparatus for providing effective respiratory therapy to a plurality of chemical warfare casualties and more particularly to apparatus for resuscitating a plurality of such patients.

In combating chemical warfare, a basic requirement is to provide each potential chemical warfare patient with an appropriate antidote, preferably in a dosage form contained within an automatic injector. Nerve agents used in chemical warfare can induce excessive airway secretions, bronchoconstriction and apnea. Therefore, in addition to antidotes, an important factor in successfully managing mass casualties resulting from nerve agent poisoning will be the ability to keep the patient breathing until he recovers sufficiently to breathe for himself.

Emergency resuscitation units have been proposed. For example, one such unit is currently marketed under the name Pneupac, produced by Pneupac Limited of London, England. Representative patents disclosing additional equipment of this type include the following: U.S. Pat. Nos. 3,191,596; 3,304,939; 3,333,603; 3,339,545; 3,515,134; 3,530,856; 4,077,404; and 4,197,843. Emergency units of this type are basically provided for use with ambulance crews under conditions which are less stringent than those encountered in chemical warfare situations.

A basic requirement in a chemical warfare situation is that the resuscitator unit should have the capability of dealing with a plurality of patients, rather than a one-on-one situation, as with the existing commercial units. That is, one-on-one resuscitators are labor intensive which will try, if not exhaust, the medical system's manpower resources. Moreover, it is important to be able to provide the patient with suitable respiratory medicaments as, for example, aerosol atropine, and in this regard it is important to provide an apparatus suitable to administer such atropine without unduly exposing the patient or disrupting the resuscitation which is being undertaken. Moreover, it is desirable to provide that the medicament be supplied in the system only during such time as the patient is being supplied with fresh air under pressure, as distinguished from other times when stale air is expelled from the patient's lungs. The use of atropine in addition to its systemic effect is important, since it promotes oxygenization by drying secretions and relieving bronchoconstriction. Its effect on the lungs can be expected to be maximal if atropine can be given in a manner that provides a high local concentration at the bronchi and mucous secreting areas of the patient's airway.

An important capability of an apparatus suitable for chemical warfare usage is the ability to continually monitor the patient's airway pressure as an indicator of incipient or already developed bronchoconstriction. Of additional significance is the provision of suction suitable to remove mucous and other secretions which can cause airway blockage.

Accordingly it is an object of the present invention to provide a plural patient resuscitator apparatus suitable for use under the exigencies of chemical warfare situations which embodies a sufficient number of the important functional capabilities noted above as to be effective.

In accordance with the principles of the present invention the apparatus preferably embodies a four-station resuscitator unit which is electrically driven either by a suitable source of AC or DC electricity or a battery, and alternatively manually driven when an electrical power source is unavailable. The resuscitator unit preferably embodies a plurality of positive displacement air chamber assemblies which are moved by a cam track through repetitive cycles, each of which includes an expanded movement and a retracted movement during a time period of less than one-half of the time period of the entire cycle. Each air chamber assembly is connected with a fresh air inlet valve through which fresh air passes during each expanded movement, a valved air line or conduit leading to a face mask assembly through which air passes during each retracted movement of the associated air chamber assembly to supply fresh air into the lungs of the patient and a stale air exhaust valve for permitting air expelled from the lungs of the patient to be exhausted to atmosphere through the associated face mask assembly.

Preferably the conduit leading to each face mask assembly has provided therein an assembly for injecting a dosage of aerosol medicament, such as atropine, into the conduit and either an indicator or an automatic mechanism is provided for insuring that the medicament dosage will be injected into the conduit only during the minor time portion of each cycle during which fresh air is being supplied to the lungs of the associated patient, thus insuring effective utilization of the medicament.

Another preferred capability which is embodied in the present apparatus in accordance with the principles of the present invention is the provision of an air suction pump, which communicates through a liquid trap or mucous collector with an air suction line extending through each face mask so as to provide the capability of accommodating mucous and other secretions which tend to block the patient's airway. The need to use such suction can be diminished by effective utilization of respiratory medicaments, particularly atropine, since atropinization tends to promote oxygenization by drying secretions and relieving bronchoconstriction. Fur purposes of providing the operator with patient information indicating bronchoconstriction, and hence the need for atropine insufflation, the apparatus of the present invention provides a pressure gauge for each face mask assembly conduit.

Another object of the present invention is the provision of an apparatus of the type described, which is simple in construction, effective in operation and economical to manufacture and maintain.

These and other objects of the present invention will become more apparent during the course of the following detailed description and appended claims.

The invention may best be understood with reference to the accompanying drawings, wherein an illustrative embodiment is shown.

Referring now more particularly to the drawings, there is shown therein an apparatus, generally indicated at 10, for resuscitating four patients simultaneously which embodies the principles of the present invention. It will be understood that while the number of patients which can be resuscitated by the use of the apparatus is shown to be four, the number could be two, three or more than four, with four being considered preferable.

As shown, the apparatus 10 includes four face mask assemblies (of which only one is shown), generally indicated at 12. Each face mask assembly 12 is connected by a valved conduit assembly, generally indicated at 14, to a central resuscitator unit, generally indicated at 16. In the broadest aspects of the present invention the resuscitator unit 16 may be a pressurized fluid actuated system, as for example, a system such as commercialized under the name Pneupak by Pneupak Limited of London, England. Preferably, however, the unit is one which is suitable to be alternatively driven by an electrical power source or operated manually in the event that an electrical power source is not available under emergency conditions. The preferred resuscitator unit 16 includes a frame or housing assembly, generally indicated at 18, which carries four bellows assemblies 20 for repetitive cycles of retracted and expanded movements by a movable or rotatable cam track assembly 22. Each bellows assembly 20 is connected with an associated valved conduit assembly 14 so that during each expanded movement of each bellows assembly 20 fresh air is drawn therein and during each retracted movement of each bellows assembly 20 air is delivered or supplied through the associated conduit assembly 14 to the associated face mask assembly 12 in such a way as to enter the lungs of a patient operatively connected with the associated face mask assembly 12. Each valved conduit assembly 14 functions to enable the lungs of the patient to be expelled of stale air during the portion of each cycle of the associated bellows assembly 20 when the air is not being supplied. Preferably, the portion of the cycle during which air is supplied takes place during a time period which is less than half of, or a minor part of the total time period of each cycle.

The frame assembly 18 of the unit 16 may assume any suitable construction, the arrangement shown in the drawings being somewhat schematic to emphasize the functional aspects of the invention rather than the structural aspects thereof. Each valved conduit assembly 14 has embodied therein a medicament aerosol injecting assembly, generally indicated at 24, and a pressure gauge 28 suitably connected to indicate the pressure within the conduit assembly adjacent each one of the four face mask assemblies 12. In addition to the above, each valve conduit assembly 14 also has associated therewith a suction line connected with a suitable source of suction so as to enable the operator to remove mucous and other secretions which may tend to interrupt the flow of air necessary to the resuscitating operation being carried out.

As shown, the frame includes upper and lower horizontally extending frame plates 44 and 46. In the embodiment shown these frame plates are fixedly secured in vertically spaced relation by three corner struts or posts 48 and four side posts 50. In the embodiment shown, the sides of the frame are open. It will be understood that panels may be provided to enclose the sides if desired. Such side panels are eliminated from the drawings for the purpose of simplicity.

Mounted within the central portion of the frame assembly 18 is a rotatable vertically extending shaft 52. Shaft 52 is suitably journaled, as by upper and lower bearing assemblies 54 and 56, to the central portion of the upper plate 44 and lower plate 46 respectively. As shown, the upper end of the shaft 52 extends above the upper plate 44 and is connected with the output shaft of a clutch assembly 58. Clutch assembly 58 is preferably any well-known commercial embodiment of an overrunning clutch assembly operable when power driven to engage two shaft sections and when manually overrun to disengage the same. The output shaft section of the clutch assembly 58 is connected with the shaft 52 as aforesaid while the input shaft thereof is connected with a gear reducer 60 which, in turn, is driven by the output shaft of an electric motor 62. Clutch assembly 58 may also be of any well known commercial embodiment of a clutch assembly which is electrically energized in conjunction with the energization of the motor to engage the output shaft of the gear reducer to the shaft 52 and when de-energized along with the electric motor 62 to disengage the shaft of the gear reducer 60 from the shaft 62 so as to permit the same to be turned manually.

As shown, the manual turning action is accomplished by means of a hand crank 64 detachably mounted on the upper end of a shaft 66 suitably journaled between the four corners of the frame plates 44 and 46 where corner posts 48 are not mounted. A motion transmitting mechanism 68 is provided between the corner shaft 66 and central shaft 52 for transmitting rotational movements imparted to the corner shaft 66 by the hand crank 64 to the central shaft 52. The motion transmitting mechanism 68 may assume any desired form. As shown, it is a simple sprocket chain and sprocket drive.

Figure 5:
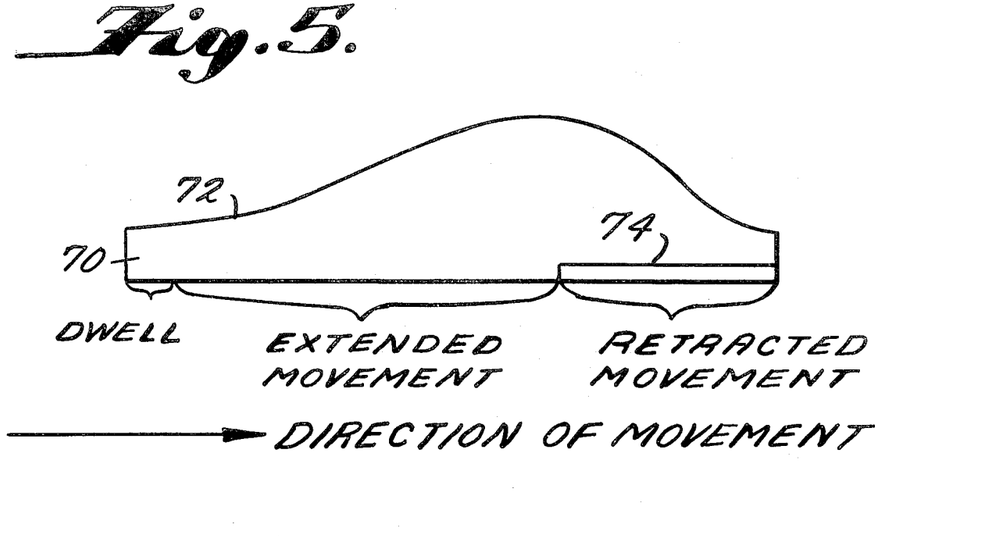
FIG. 5 is a development of the cam surface of the cam track.

The cam track assembly 22 is in the form of a rotary cam track structure 70 of generally cylindrical exterior configuration having a flanged upwardly facing cam track surface 72 formed along the upper exterior periphery thereof. As best shown in FIG. 5, the cam track surface consists essentially of a first semisinuous or half sine wave portion having an angular extent of approximately 120°, a second semisinuous or half sine wave portion having an angular extent of approximately 220°, and a dwell portion of approximately 20°. Preferably, the first semisinuous portion defines a simple harmonic motion representing the retracted movement of the associated bellows assembly 20 and the second portion represents a simple harmonic motion of expanded movement of the associated bellows assembly 20. It will be understood that in considering the entire cam track surface as the equivalent of one cycle of movement consisting of 360° of travel, the portion representing the retracted movement of the associated bellows assembly is approximately 120° or a one-third portion of the entire cycle in terms of degrees or time assuming a uniform rotational movement. It will be understood that the cam track surface could be divided into a dwell portion and a simple harmonic motion portion, or the cam track surface may include a semisinuous curvature for the retracted movement within the initial 120°, with the other 240° being a semisinuous curve of a frequency twice that of the first semisinuous curve.

In FIG. 5 the 120° portion which is operable to accomplish the retracted movement of the associated bellows assembly is represented by the portion indicated by brackets. This portion of the cam track structure 70 is also shown as including a switch actuated projecting surface 74 which may be provided for a purpose hereinafter to be more fully explained. The cam track structure 70 cooperates with four cam follower assemblies 78, each of which includes a hollow cylindrical member 80 having a roller 82 journaled outwardly from one side thereof which rollingly engages the cam track surface 72. Each member 80 extends vertically in a parallel direction in relation to the shaft 52 and has its hollow interior slidably mounted on a shaft 84 fixed on the lower housing plate 46.

A coil spring 85 is connected between the outer end portion of member 80 and the lower plate 46 so as to resiliently urge the member downwardly so that the associated roller 82 thereof is biased to engage the cam track surface 72.

In order to provide for selective variation in the amount of expanded and retracted movement of each bellows assembly 20, a vertically movable stroke adjusting member 86 is mounted on each side post 50 in a position to engage the bottom of a plate 88 fixed to the upper end of the associated member 80. Each plate 88 forms a part of the associated bellows assembly 20 which also includes an annular accordian folded flexible bellows member 90 having its lower fold suitably fixed to the upper surface of the associated plate 88. Each bellows member 90 is preferably of rectangular configuration with rounded corners and has its upper fold suitably sealingly secured to the lower surface of the upper frame plate 44.

Each adjusting member 86 is moved vertically into a desired position of adjustment by a shaft 92 suitably journaled between the upper and lower frame plates 44 and 46. Each shaft 92 is threaded between its ends and is engaged within an interiorly threaded opening extending through the associated adjusting member 86 so that the latter is moved vertically in response to turning movements of the shaft. The turning movement of each shaft 92 is facilitated by the provision of a manually engageable knob 94 on the end thereof extending above the upper frame plate 44. If desired a pair of nuts 96 may also be threadedly mounted on each shaft 92 on opposite sides of the associated member 86 to limit the extent of adjustment thereof.

Figure 1:
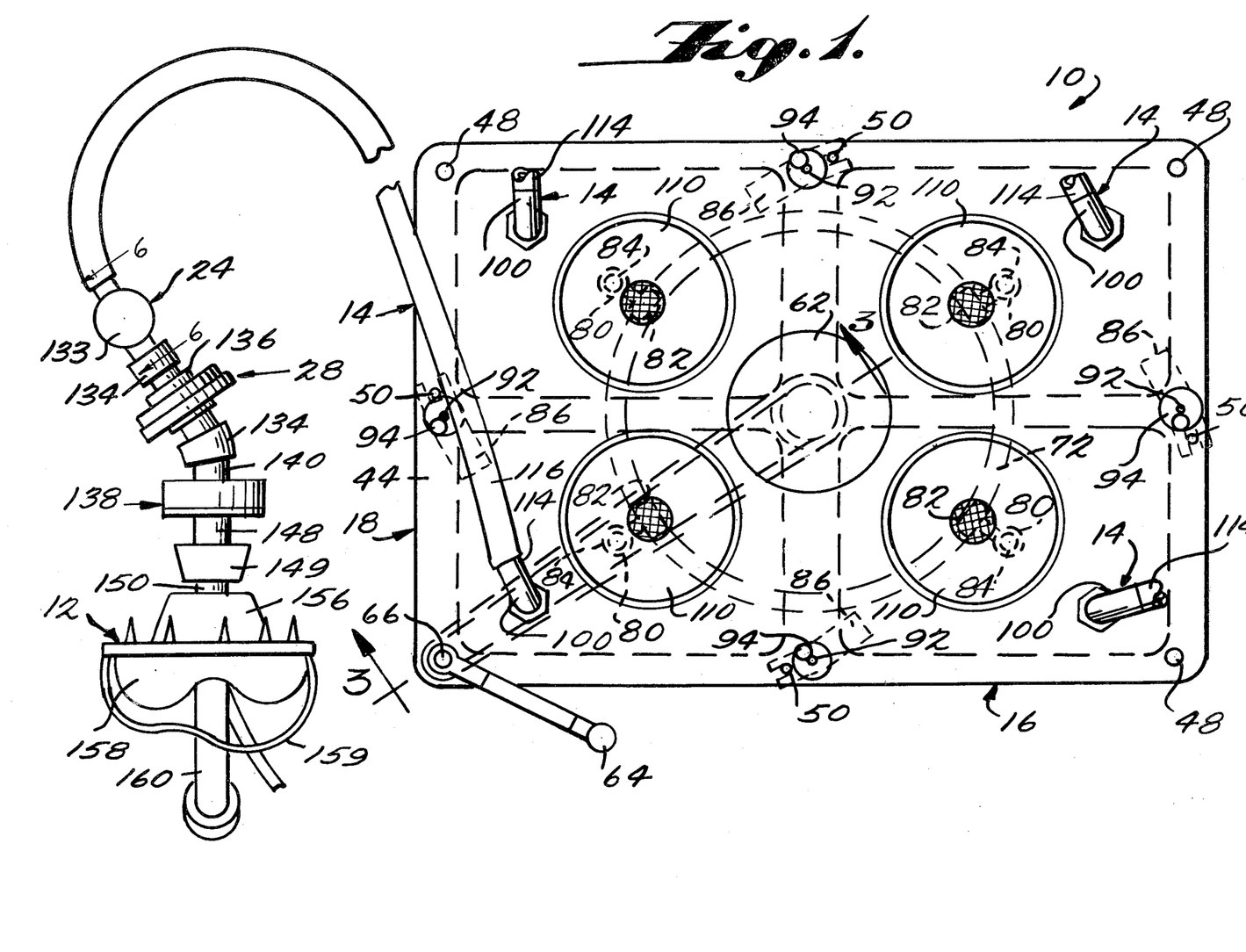
FIG. 1 is a top plan view with certain parts broken away for purposes of clearer illustration of a plural patient resuscitator apparatus embodying the principles of the present invention.
Figure 2:
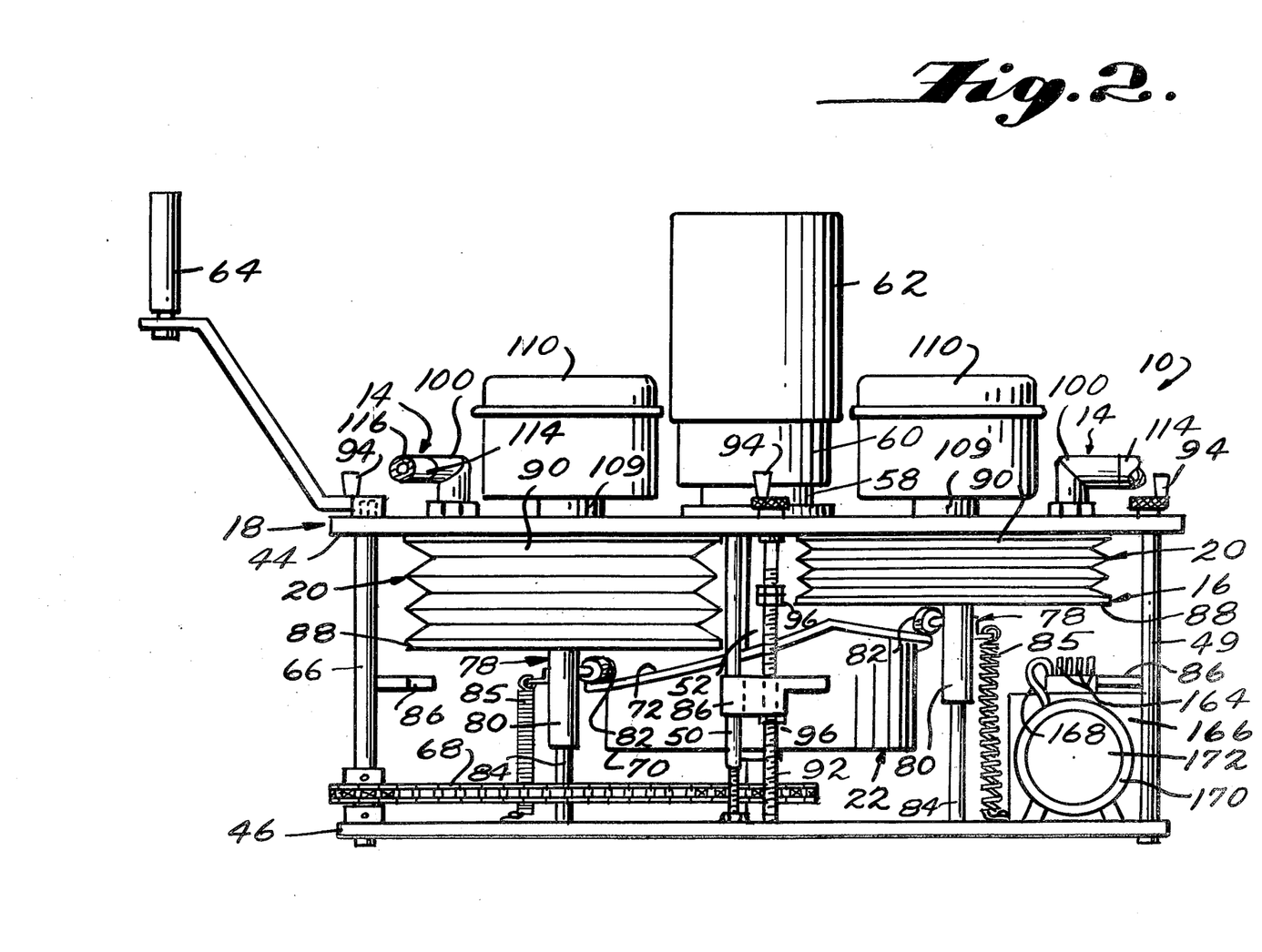
FIG. 2 is a front elevational view of the apparatus shown in FIG. 1 with certain parts broken away for purposes of clearer illustration.
Figure 3:
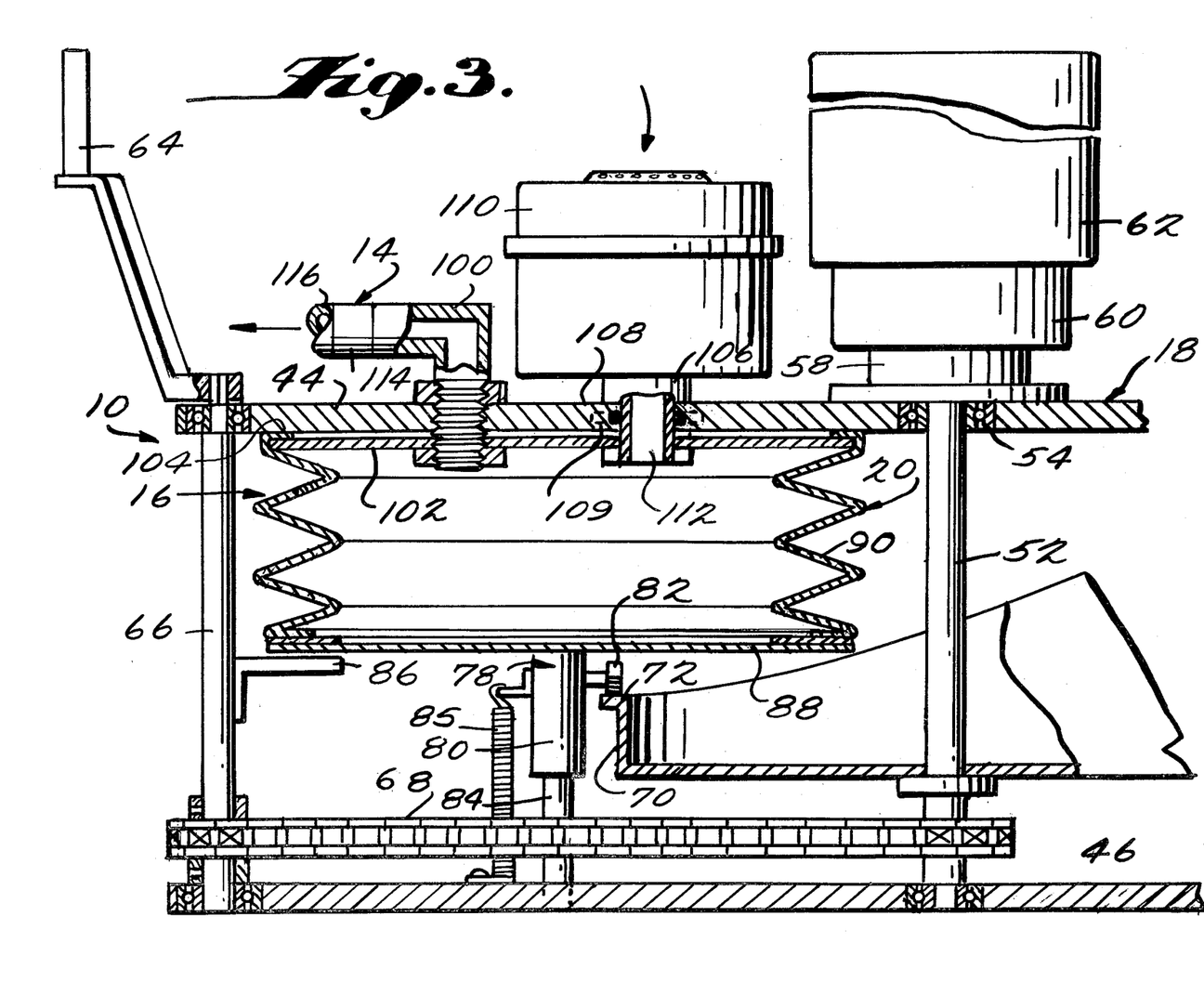
FIG. 3 is an enlarged fragmentary vertical sectional view taken along the line 3—3 of FIG. 1 showing the cam track mechanism moving the same into a fully retracted position.

As best shown in FIG. 3, each valved conduit assembly 14 includes an L fitting 100, one end of which is adapted to communicate with the interior of associated bellows member 90. The upper end of each bellows member 90 is fixed to the upper plate 44 by an apertured plate 102 over which each bellows member 90 extends with each bellows member providing an upper annular inturned flange 104 which is engaged between the upper plate 44 and the apertured plate 102 (see FIG. 3). Formed in the upper plate 44 is a vertical opening 106 suitably grooved to receive an O-ring seal 108. The opening 106 and O-ring seal 108 are sized to receive and seal against the exterior periphery of an output pipe 109 of a filter cartridge 110 which pipe 109 also extends through a registering opening in the plate 102 so as to communicate with the interior of the associated bellows. Each pipe 109 has a check valve 112 mounted therein for permitting flow of air through the filter cartridge 110 into the pipe 109 but preventing flow in the opposite direction. The opposite end of the L fitting 100 has formed therein a check valve 114 which permits flow outwardly thereof but prevents flow in the opposite direction. Each valve conduit assembly 14 also includes a section of flexible conduit 116 connected with check valve 114 or with the end of the L fitting 100 in which the check valve 114 is mounted. As shown, the opposite end of each conduit section 116 leads to the medicament injecting assembly 24.

Figure 4:
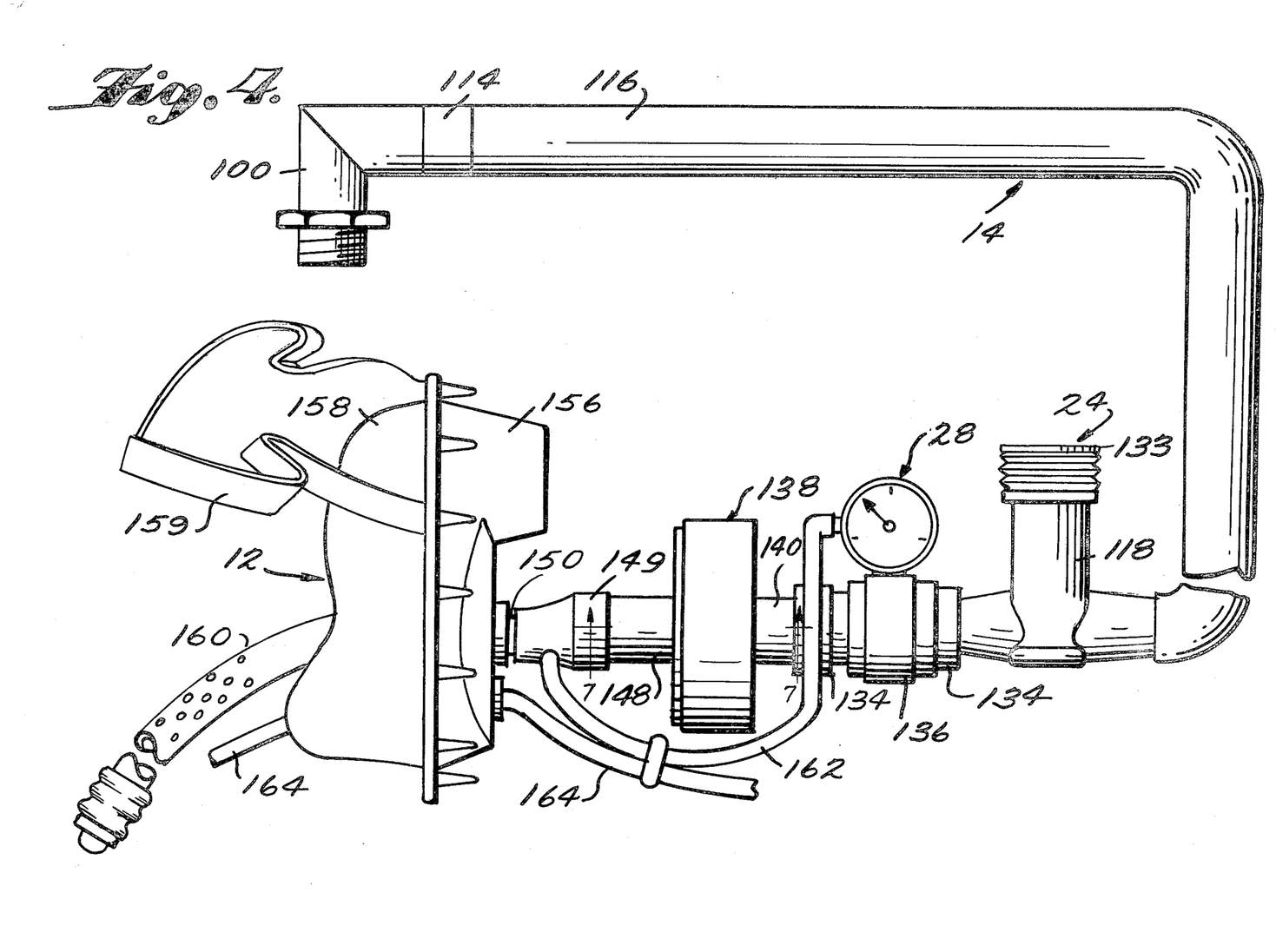
FIG. 4 is a fragmentary side elevational view with parts broken away for purposes of clearer illustration showing the communication of the air delivered by one of the bellows assemblies of the apparatus to the associated face mask assembly.
Figure 6:
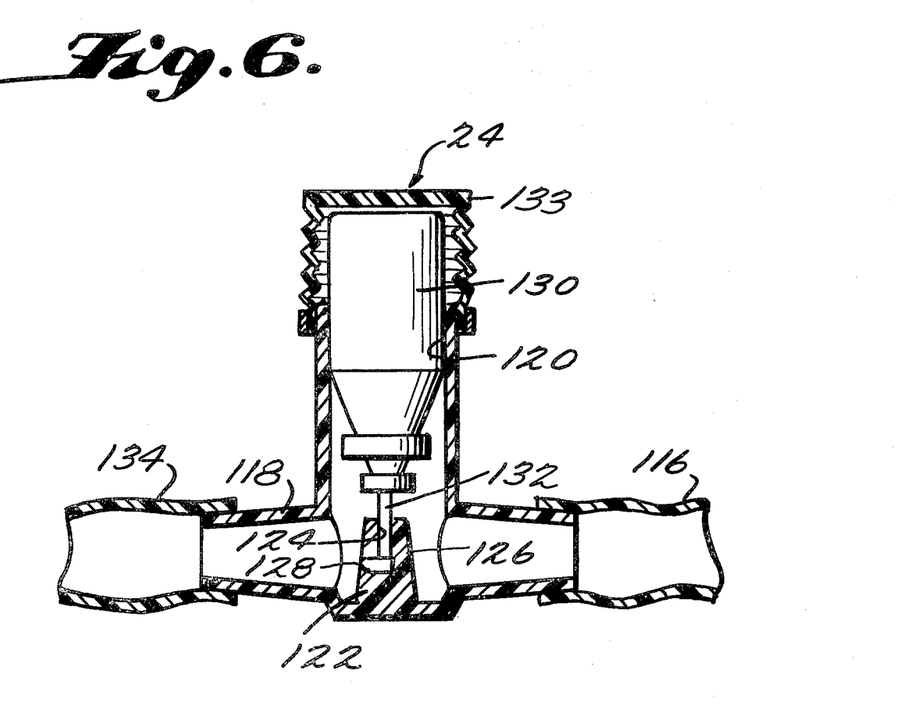
FIG. 6 is an enlarged fragmentary sectional view taken along the line 6—6 of FIG. 1.

As best shown in FIGS. 4 and 6, each medicament injection assembly 24 includes an inverted T-shaped tubular section 118 having an opening 120 in the upper end of the stem thereof. Formed on the interior of the tubular section 118 in axial alignment with the opening 120 is a rod-like projection 122. Projection 122 has a central opening 124 extending downwardly therein terminating at its forward edge in an abutment 126 and at its rearward portion with an L-shaped opening which terminates in a discharge orifice 128 aligned axially with the tubular section 118. Mounted for sliding movement within the opening 120 is an aerosol medicament container 130 having a tubular valve stem 132 extending therefrom of a size to engage within the central opening 124 in the projection 122. The container 130 is detachably sealed within the T-shaped section 118 for vertical movement as by a bellows structure 133. The container 130 with its valve stem 132 is constructed in accordance with the teachings contained within U.S. Pat. No. 2,968,427, the disclosure of which is hereby incorporated by reference into the present specification. A commercial embodiment of the same is marketed under the trademark MEDIHALER ® by Riker Laboratories, Inc. It will be understood that the container 130 includes an amount of a suitable respiratory medicament, as for example, atropine, which is equal to a multiplicity of dosages.

Figure 7:
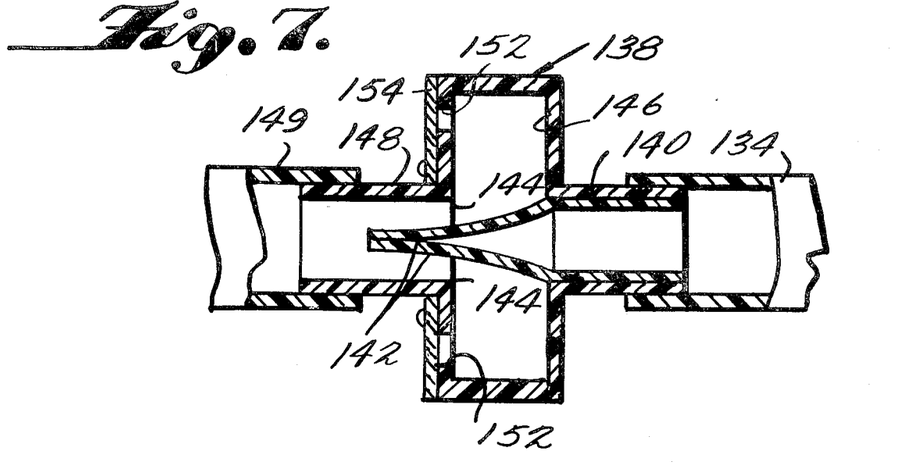
FIG. 7 is an enlarged fragmentary sectional view taken along the line 7—7 of FIG. 4.

The outlet or downstream end of the tubular section 118 is connected with a second conduit section 134 within which is mounted a pressure relief valve 136. The pressure relief valve 136 may be of any suitable design and preferably is one of those commercially available suitable to relieve the pressure within the associated conduit assembly by opening to atmosphere when a pressure equivalent to approximately 65 cm of water is reached. Conduit section 134 leads to a stale air exhaust valve assembly 138. Valve assembly 138 is also preferably of known design, the exemplary embodiment shown is illustrated somewhat schematically in FIGS. 4 and 7 as including a housing having a tubular inlet 140 which is connected with the conduit section 134. Inlet 140 leads to a pair of cooperating flap valve elements 142 which are normally biased together but are capable of being moved apart when pressure is communicated with the inlet 140. When the flap valve elements are moved apart their exterior surfaces engage a pair of valve seats 144 which lead to an annular chamber 146 provided by the housing. The housing of the valve assembly also includes an outlet 148 which communicates with the central portion of the flap valves 142 downstream of the valve seats 144 and is adapted to engage and seal within an adaptor 149 which, in turn, is sealed within an opening 150 in the face mask assembly. Annular chamber 146 includes exhaust openings 152 which are closed by an annular flap 154 forming with the association annular portion of the housing defining the opening 152 an exhaust check valve.

The term face mask assembly as herein utilized comprehends within its meaning a simple face mask of the type suitable to fit over the mouth and nose area of a wearer such as is utilized in emergency treatments or it may be a more elaborate arrangement such as embodied in conventional gas masks. An exemplary embodiment of an emergency type face mask is the one marketed as a part of the Esophogeal Airway manufactured by Brunswick Manufacturing Company, Inc. and distributed by the assignee company of the present application. The salient features of the Brunswick product are disclosed in U.S. Pat. Nos. 3,683,908 and 3,841,319, the disclosures of which are hereby incorporated by reference into the present specification. Suffice it to say that the face mask assembly 12 includes a face mask element 156 which contains opening 150 in the central portion thereof, the face mask element 156 having an air actuated peripheral seal 158 extending therearound so as to provide a seal for the face of the wearer. Preferably, the face mask is provided with a harness 159 enabling the operator to operatively connect the same with the patient in retained relation. It will be understood that the face mask may be used with an optional esophogeal obturator tube 160, such as disclosed in the aforesaid patents, for the purpose of insuring against regurgitation of the contents of the stomach of the patient while providing for an unobstructed airway for the patient through the face mask.

Each valve conduit assembly 14 also includes a pressure sensing line 162 which extends through the conduit adaptor 149 at a position adjacent the associated face mask so as to sense the pressure condition therein. The opposite end of each line 162 is communicated with the pressure gauge 28. Each conduit assembly 14 also has associated therewith a suction line 164. Suction line 164 extends through the face mask element 156 in sealed relation therewith so as to be in a position within the interior of the face mask to be disposed within the throat of the patient and provide for suction of mucous or other secretions which may accumulate therein and tend to provide a block to the flow of air to and from the patient's lungs.

Each suction line 164 leads to a liquid trap 166 suitably carried on the main frame assembly 18 of the resuscitator unit 16. Extending from the liquid trap 166 is a suction pump line 168 which, in turn, extends to the interior of a suction pump assembly, generally indicated at 170. Suction pump assembly 170 may be of any suitable construction of the type adapted to be power driven. As shown an electric motor 172 is provided to power the pump assembly 170. It will be understood that other suction sources may be provided if desired including suction sources capable of manual operation or alternative manual or power operation. In the embodiment shown, evacuation of the liquid trap 166 serves to create a suction in each of the suction lines 164 connected in parallel. It can be seen that by providing a single pump assembly 170 connected with a single liquid trap 166, a continuous suction source or supply is available to each of the suction lines 164 at all times.

Figure 8:
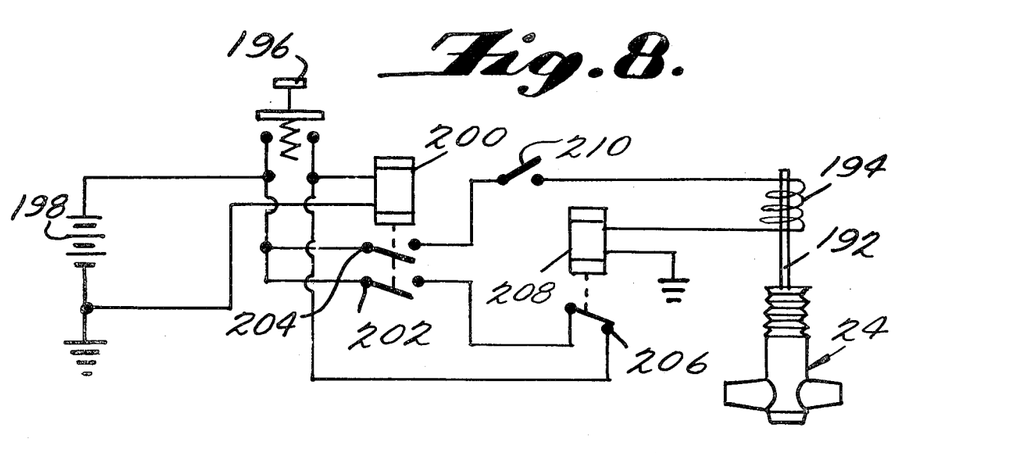
FIG. 8 is a schematic wiring diagram illustrating a modified form of electrical circuitry for automatically actuating the medicament injecting assembly at the proper time within the respiratory cycle.

FIG. 8 illustrates a modification for replacing the manual actuation of the medicament injecting assemblies 24 and pressure indicators 28 with a manually initiated automatic actuation. FIG. 8 illustrates the automatic circuitry for one medicament injecting assembly 24, it being understood that the circuitry shown can be triplicated for the other three medicament injecting assemblies 24. As schematically shown in FIG. 8, a solenoid plunger 192 is mounted in a position to operate the medicament injecting assembly 24 when an associated solenoid coil 194 is energized. A manually actuated switch 196 is provided which is normally spring biased into an open position and is connected so that when it is manually closed a circuit is completed across a power source 198 through a coil 200 of a latched relay having two normally open switches 202 and 204. Normally open switch 202 when closed provides a holding circuit for the relay coil 200 and is connected in a circuit capable of short circuiting the switch 196 in series with a normally closed switch 206 of a reset relay having a coil 208. Normally open switch 204 of the latched relay is connected across the power source 198 in series with solenoid coil 194, a normally open cam actuated switch 210, and the coil 208 of the reset relay. Switch 210 replaces light switch 76 previously described. Switch actuating structure 74 previously described is preferably shortened so as to close the switch 210 only during the initial 50% of the associated bellows assembly 12 retracted movement which constitutes the optimum time for medicament injection.

Figure 9:
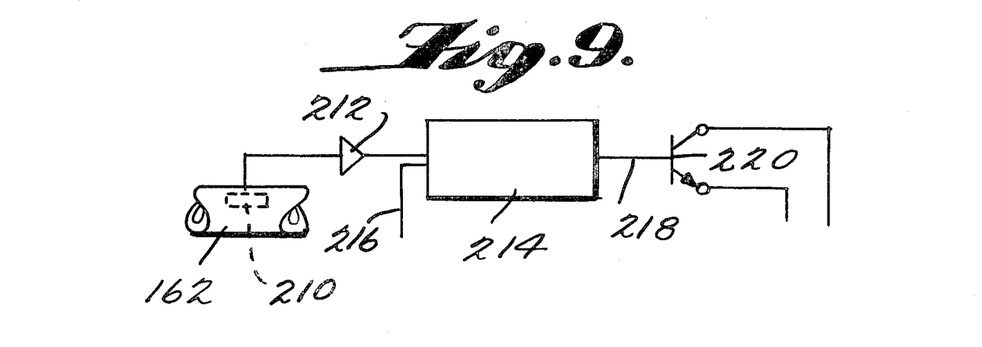
FIG. 9 is a fragmentary schematic wiring diagram illustrating a modification of the electrical circuitry shown in FIG. 8 for automatically actuating the medicament injecting assembly at the proper time within the respiratory cycle in response to the sensing of a predetermined pressure condition within the respiratory system of the patient.

Referring now more particularly to FIG. 9, there is shown therein a modification of the circuitry illustrated in FIG. 8 wherein the selective manual capability of the actuating switch 196 is replaced by an automatic actuating capability responsive to the presence of a predetermined pressure condition within the associated face mask assembly 12. To this end a pressure transducer 211 is communicated with each line 162. The electrical output of the pressure transducer 211 is communicated through an amplifier 212 to a level detector or comparator 214. The level detector 214 has a reference voltage communicated therewith through line 216 so as to provide an electrical output in a line 218 when the voltage from the amplifier 212 is above the reference voltage in line 216. For example, the detected or compared voltage level could be that which would correspond with the electrical output of the transducer 211 when the pressure in line 162 is 45 cm of water. The electrical output of line 218 is connected with a transistor 220 which is connected in the circuit of FIG. 8 in the same manner as manual switch 196. It will be understood that the circuitry shown in FIG. 8 may likewise be made up of solid state components rather than the mechanical type components schematically shown therein.

The apparatus 10 of the present invention is particularly adapted for use under chemical warfare emergency conditions. As previously indicated, in addition to providing automatic injectors having a nerve gas antidote dosage therein, it is important to alleviate the symptoms which are induced by nerve agent exposure, such as excessive airway secretions, broncho-constriction, and apnea. The face mask 12 described above is not disclosed as including the usual shrouds which are usually associated with gas masks. It will be understood that such a shroud could be readily provided or alternatively the face mask assembly 12 could be replaced by a conventional gas mask assembly. Connection to the conventional gas mask may be effected in a variety of different ways depending upon whether or not the gas mask assembly is of a type in which the air intake filter is on the exterior or interior of the gas mask. Where the air inlet is on the exterior, one simple method of attaching the present valve conduit assembly 14 therewith is to provide a T connection with the adaptor 149 downstream of the stale air exhaust valve assembly 138 and connecting one branch of the T over the exhaust valve of the gas mask and the other over the second inlet of the gas mask which is not in use by having an inlet filter connected therewith. Alternatively, where interior filters are provided the exhaust valve assembly of the gas mask can be removed and the adaptor 149 of the conduit assembly 14 connected therewith.

Also in connection with the above description, mention has been made both of a mucous suction line 164 and an esophogeal obturator tube 160. Generally speaking, these two instrumentalities are provided for use in the alternative. That is, where conditions permit the installation of the obturator tube 160 within the patient the suction line can be dispensed with. On the other hand, since the suction line is simpler to install its use is preferable under chemical warfare emergency conditions, in which case the obturator tube 160 can be suitably eliminated.

In either event, it will be understood that the initial procedure in the operation of the apparatus 10 is to connect the patient operatively with the face mask assembly 12. With regard to resuscitation it will be noted that the unit 16 is preferably operated by a source of AC current suitably energizing the electric motor 62 through an appropriate rectifier or alternatively by a battery. Where a source of electricity is not available, crank 64 may be turned to effect the operation of the resuscitator unit 16. It will be noted that the rotational movement of the shaft 52 carries with it the cam track assembly 22 so that cam track surface 72 acting through rollers 82 will cause members 80 to oscillate which, in turn, causes the associated bellows assemblies 20 to be moved through successive cycles of retracted movement and expanded movement. The retracted movement takes place in approximately one-third the total time of each cycle and serves to deliver air through the associated conduit assembly 14 and face mask assembly 12 to the lungs of the patient. During the remaining time of each cycle, the air delivered to the patient's lungs is expended through the face mask assembly 12 and outwardly to the atmosphere through the operation of the stale air exhaust valve assembly 138. In this regard, it will be noted from FIG. 7 that when pressure is flowing through the conduit assembly 14 into the stale air exhaust valve assembly 138, pressure access to the exhaust check valve 154 is closed off by the engagement of the flap valve elements 142 with the valve seats 144. When the pressure from conduit assembly 14 is no longer being delivered, the flap valve elements 142 move away from the seats 144 enabling air from the end 148 of the valve assembly 138 to be exhausted to atmosphere past the valve seat 144 and flap valve elements 142, into the chamber 146 and out of the exhaust openings 152 through the check valve 154.

The cam track surface 72 is shaped with respect to the capacity of each bellows assembly 20 so as to provide a tidal volume during each retracted movement of approximately 900 ml. The 900 ml is exemplary and the actual tidal volume provided may vary within a range of 50 ml to 1500 ml. A preferred setting for the limiting nuts 96 is one which provides a range of 600 ml to 900 ml. The motor 68 and gear reducer 66 are set to provide a rotational speed sufficient to cycle each bellows assembly 20 at a frequency of approximately 16 cycles per minute. Here again the 16 cycles per minute is exemplary and the actual cycles per minute may vary within the range of 7 to 25 cycles per minute. As previously indicated the shape of the cam surface 72 is such that the time for the retracted movement is approximately $33\frac{1}{3}\%$ of the total cycle time. Here again, the $33\frac{1}{3}\%$ of the total cycle time is exemplary and the actual percentage may vary within the range of 25% to 50%.

It will be understood that by suitably adjusting the bolts 96 upwardly, the tidal volume per cycle can be reduced with a commensurate reduction in the $33\frac{1}{3}\%$ during which the retracted movement takes place. Moreover, as previously indicated, the relief valve assembly 136 within each conduit assembly 14 is preferably set to limit or prevent the pressure within the conduit assembly from exceeding a value of 65 cm of water.

With the above in mind, the operator by viewing the pressure gauges can determine whether the associated patient has a bronchoconstrictive condition, indicating the desirability of administering a dosage of atropine. When the operator determines that an injection of atropine is desirable, the operator simply watches the pressure gauge to determine when it rises during the retracted movement of the associated bellows assembly. As soon as the rise in pressure comes, the operator manually actuates the associated medicament injecting assembly 24 by pressing down on the top of the bellows 133 which has the effect of moving the container 30 downwardly with respect to the valve stem 132 disposed against stop 126. This movement releases a single measured dosage of aerosol medicament from the valve stem 132 which passes outwardly of the orifice 128 into the center of the downstream branch of the T fitting 118. By carefully timing the actuation of the assembly 24 with the onset of the rise in pressure, the introduction of the aerosol medicament into the air being delivered to the patient is insured.

Where the automatic circuitry of FIG. 8 is provided, the operator simply depresses the button 196 and immediately releases the same. The momentary closing of button switch 196 completes the circuit to the coil 200 of the latched relay which, in turn, completes a circuit to the solenoid coil 194 in the event that the associated bellows assembly is in the initial portion of its retracted movement of its cycle, since the associated cam operated switch 210 will then be closed. The energization of solenoid coil 194 causes solenoid plunger 192 to move downwardly which has the effect of actuating the medicament injecting assembly 24 in the manner previously described. The energization of the solenoid coil 194 also energizes the series connected coil 208 of the reset relay which has the effect of disrupting the holding circuit for the latched relay 200. In the event that during the instant that button 196 is pushed the associated bellow assembly 20 is not in the initial portion of its retracted movement in its cycle, solenoid coil 194 will not be energized due to the associated cam operated switch 210 being open. The latched relay, however, is latched or held in an energized condition by virtue of the holding circuit associated with the reset relay so that during the onset of the next retracted movement of the associated bellows assembly 20 switch 210 will be closed, thus energizing the solenoid coil 194 and effecting operation of the medicament injecting assembly 24 in the manner previously described. It can thus be seen that with the arrangement shown in FIG. 8, the operator in order to achieve the injection of a single dosage of medicament in proper timed relation need only depress the button 196 momentarily and the dosage will be delivered at the onset of the delivery of air to the patient's lungs.

Where the automatic circuitry of FIG. 9 is additionally provided in the circuitry of FIG. 8, it will be understood that the energization of the solenoid coil 194 which serves to actuate the injector 24 will be automatically accomplished when a predetermined pressure condition within the associated face mask assembly 12 is sensed by the pressure transducer 211. For example, where a pressure of 45 cm of water exists within the associated pressure line 162 the amplified voltage output of the pressure transducer 211 will exceed the reference voltage in line 216 communicated with comparator 214 so that the output in line 218 thereof causes the transistor 220 to complete the circuit of FIG. 8 in the same way that the circuit of FIG. 8 is completed by closing manual switch 196.

The term "fresh air" as herein used contemplates either uncontaminated atmospheric air, contaminated atmospheric air which has been filtered, bottled air, or a bottled air substitute such as bottled oxygen.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. Apparatus for resuscitating a plurality of patients comprising
    a plurality of face mask assemblies each of which is operable to be operatively connected with a patient so as to permit fresh air to be supplied to the lungs of such patient,
    means for delivering successive volumes of fresh air under pressure to each of said face mask assemblies at a desired cyclical frequency wherein each cycle includes said fresh air delivery as a minor part thereof,
    stale air exhaust valve means for permitting air expelled from the lungs of each patient during the remaining major part of each cycle associated therewith to be exhausted to atmosphere through the associated face mask assembly,
    means operatively associated with each face mask assembly for selectively supplying a respiratory medicament dosage into the fresh air delivered to each face mask assembly, and
    means operatively associated with each face mask assembly for indicating a minor part of each cycle associated therewith during which fresh air is delivered thereto so that the associates selective medicament delivering means is selected to deliver medicament only during the minor cycle part when said fresh air is delivered,
    said fresh air delivering means comprising a frame,
    a plurality of expandable and retractable positive displacement air chamber assemblies carried by said frame,
    cam track means movably carried by said frame,
    means for operatively connecting said cam track means with each of said air chamber assemblies so that each air chamber assembly is moved during the movement thereof through repetitive cycles each of which includes an expanded movement and a retracted movement during a time period of less than one-half of the time period of the entire cycle,
    fresh air inlet check valve means for controlling the flow of fresh air into each air chamber assembly during each expanded movement thereof,
    means for conducting fresh air from each of said air chamber assemblies to an associated face mask assembly during each retracted movement of the associated air chamber assembly and for preventing air flow therebetween in the opposite direction,
    means for moving said cam track means so that each of said air chamber assemblies is moved through repetitive cycles each of which includes (1) an expanded movement to cause fresh air to flow therein past the associated fresh air inlet check valve means and (2) a retracted movement during the aforesaid less than one-half cycle time period to cause fresh air therein to flow therefrom through the associated face mask assembly into the lungs of a patient operatively connected therewith so as to be expellable from the lungs of the patient through the associated face mask assembly and past the associated stale air exhaust valve means during the greater than one-half cycle time period when the associated air chamber assembly is not being moved through a retracted movement.

2. Apparatus as defined in claim 1 wherein each face mask assembly has operatively associated therewith in a position to be observed by an operator means for indicating the operative pressure adjacent the face mask assembly so as to enable the operator to readily determine a bronchoconstrictive condition of a patient operatively connected with the associated face mask assembly.

3. Apparatus as defined in claim 1 or 2 including suction pump means providing a source of fluid under negative pressure, a mucous suction line for each face mask assembly having an inlet end adapted to be extended within the mouth of a patient operatively connected therewith, and means for communicating said suction pump means with each of said suction lines including means for collecting mucous entering the inlet of each suction line before the same reaches the suction pump means.

4. Apparatus as defined in claim 1 or 2 wherein each face mask assembly has operatively associated therewith pressure relief valve means operable to relieve the pressure adjacent the associated face mask assembly in such a way as to prevent such pressure from exceeding a predetermined value.

5. Apparatus as defined in claim 1 or 2 wherein said cam track means is mounted for rotational movement and said moving means comprises an electric motor, clutch means for engaging and disengaging said electric motor with said rotatable cam track means and hand crank means for manually rotating said rotatable cam track means when said clutch means is operable to disengage said electric motor therefrom.

6. Apparatus as defined in claim 1 or 2 including means for adjusting the volume of fresh air under pressure delivered to each of said face mask assemblies by said fresh air delivery means during each cycle thereof.

7. Apparatus as defined in claim 6 wherein each volume adjusting means includes an adjusting member engageable with the associated air chamber assembly to limit the extent of the expandable movement thereof, a fixed elongated guide slidably supporting said adjusting member for adjusting movement therealong, a turnable member threadedly engaged with said adjusting member in parallel relation with said elongated guide and a knob on said turnable member for turning the same.

8. Apparatus as defined in claim 1 wherein each selective medicament supplying means is manually selective and each minor part cycle indicating means includes a pressure gauge in a position to be observed by an operator positioned to manually select the associated selective medicament supplying means.

9. Apparatus as defined in claim 1 wherein each selective medicament supplying means includes means for selectively actuating the same and each indicating means includes means for preventing actuation of said selective actuating means during time periods other than said fresh air delivery time periods so as to insure that supply of the medicament will take place only during a time period when fresh air delivery into and through said face mask assembly is taking place.

10. Apparatus as defined in claim 9 wherein each selective actuating means comprises a manually actuatable switch.

11. Apparatus as defined in claim 9 wherein each selective actuating means comprises a switch actuated automatically in response to the presence of a predetermined pressure condition within the associated face mask assembly.

12. A plural station resuscitator unit comprising
a frame,
a plurality of expandable and retractable positive displacement air chamber assemblies carried by said frame,
cam track means movably carried by said frame,
means for operatively connecting said cam track means with each of said air chamber assemblies so that each air chamber assembly is moved during the movement thereof through repetitive cycles each of which includes an expanded movement and a retracted movement during a time period of less than one-half of the time period of the entire cycle,
a plurality of face mask assemblies each of which is operable to be operatively connected with a patient so as to permit fresh air to be supplied to the lungs of such patient,
fresh air inlet check valve means for controlling the flow of fresh air into each air chamber assembly during each expanded movement thereof,
means for conducting fresh air from each of said air chamber assemblies to an associated face mask assembly during each retracted movement of the associated air chamber assembly and for preventing air flow therebetween in the opposite direction,
stale air exhaust valve means for permitting air expelled from the lungs of a patient to be exhausted to atmosphere through the associated face mask assembly, and
means for moving said cam track means so that each of said air chamber assemblies is moved through repetitive cycles each of which includes (1) an expanded movement to cause fresh air to flow therein past the associated fresh air inlet check valve means and (2) a retracted movement during the aforesaid less than one-half cycle time period to cause fresh air therein to flow therefrom through the associated face mask assembly into the lungs of a patient operatively connected therewith so as to be expellable from the lungs of the patient through the associated face mask assembly and past the associated stale air exhaust valve means during the greater than one-half cycle time period when the associated air chamber assembly is not being moved through a retracted movement.

13. A unit as defined in claim 12 wherein said plurality of air chamber assemblies are four bellows assemblies fixed at their upper ends to said frame with their axis disposed generally vertically in annularly spaced relation about a central vertical axis.

14. A unit as defined in claim 13 wherein said cam track means includes an upwardly facing annular cam track surface formed on a cylindrical member mounted for rotational movement about said central vertical axis in a position below said bellows assemblies.

15. A unit as defined in claim 14 wherein said connecting means includes a member associated with each bellows assembly mounted with respect to said frame for vertical translational movement, a roller carried by each member in rolling engagement with said cam track surface and a plate between the upper end of each member and the lower end of the associated bellows assembly.

16. A unit as defined in claim 15 wherein said connecting means further includes a spring connected between each member and said frame for biasing said member in a direction to engage the roller thereof with said cam track surface, and adjustable stop means carried by said frame in association with each plate for adjustably limiting the downward movement of said member and hence the extent of the expanded and retracted movements of the associated bellows assembly.

17. A unit as defined in claim 16 wherein each adjustable stop means comprises an adjusting member engageable with the associated air chamber assembly to limit the extent of the expandable movement thereof, a fixed elongated guide slidably supporting said adjusting member for adjusting movement therealong, a turnable member threadedly engaged with said adjusting member in parallel relation with said elongated guide and a knob on said turnable member for turning the same.

18. A unit as defined in claim 12, 13, 14 or 15 including means for adjusting the extent of the expanded and retracted movements of each of said air chamber assemblies during each cycle of movement thereof.

19. A unit as defined in claim 18 wherein each adjusting means comprises an adjusting member engageable with the associated air chamber assembly to limit the extent of the expandable movement thereof, a fixed elongated guide slidably supporting said adjusting member for adjusting movement therealong, a turnable member threadedly engaged with said adjusting member in parallel relation with said elongated guide and a knob on said turnable member for turning the same.

20. A unit as defined in claim 12, 13, 14, 15, 16 or 17 including suction pump means providing a source of fluid under negative pressure, a mucous suction line for each face mask assembly having an inlet end adapted to be extended within the mouth of a patient operatively connected therewith, and means for communicating said suction pump means with each of said suction lines including means for collecting mucous entering the inlet of each suction line before the same reaches the suction pump means.

21. A unit as defined in claim 12, 13, 14 15, 16 or 17 wherein said cam track means is mounted for rotational movement and said moving means comprises an electric motor, clutch means for engaging and disengaging said electric motor with said rotatable cam track means and hand crank means for manually rotating said rotatable cam track means when said clutch means is operable to disengage said electric motor therefrom.

* * * * *

UNITED STATES PATENT AND TRADEMARK OFFICE
CERTIFICATE OF CORRECTION

PATENT NO. : 4,452,241

DATED : June 5, 1984

INVENTOR(S) : Stanley J. Sarnoff; William R. Tarello; Claudio Lopez, Rudolph S. Malooley It is certified that error appears in the above-identified patent and that said Letters Patent is hereby corrected as shown below:

In the cover page of the patent, column 1, after the line in which appears the following: "[22] Filed: Jun. 1, 1982" insert the following: --[63] Continuation-in-part of Ser. No. 272,972, June 12, 1981, now abandoned.--

In the specification, column 1, after the line containing the legend "PLURAL STATION RESUSCITATOR", insert the following paragraph --This application is a continuation-in-part of Ser. No. 272,972, filed June 12, 1981, now abandoned.--

Signed and Sealed this

Eighth Day of January 1985

[SEAL]

Attest:

Attesting Officer

GERALD J. MOSSINGHOFF

Commissioner of Patents and Trademarks